US008043863B2

(12) United States Patent
Bosques et al.

(10) Patent No.: US 8,043,863 B2

(45) Date of Patent: Oct. 25, 2011

(54) MS METHODS TO EVALUATE GLYCANS

(75) Inventors: Carlos J. Bosques, Arlington, MA (US); Nathaniel J. Washburn, Belmont, MA (US); Xiangping Zhu, North Grafton, MA (US); Ian Christopher Parsons, Belmont, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 20 days.

(21) Appl. No.: 12/595,894

(22) PCT Filed: Apr. 15, 2008

(86) PCT No.: PCT/US2008/060334

§ 371 (c)(1), (2), (4) Date: Feb. 9, 2010

(87) PCT Pub. No.: WO2008/128221

PCT Pub. Date: Oct. 23, 2008

(65) Prior Publication Data

US 2010/0133430 A1 Jun. 3, 2010

Related U.S. Application Data

(60) Provisional application No. 60/923,677, filed on Apr. 16, 2007.

(51) Int. Cl.
*G01N 24/00* (2006.01)

(52) U.S. Cl. ............ 436/174; 436/173; 702/19; 702/22; 702/23; 702/32

(58) Field of Classification Search .................. 436/173, 436/174; 702/19, 22, 23, 32
See application file for complete search history.

(56) References Cited

U.S. PATENT DOCUMENTS

| | | |
|---|---|---|
| 7,138,228 B2 | 11/2006 | Burlingame et al. |
| 2006/0057638 A1 | 3/2006 | Bosques et al. |
| 2006/0127050 A1 | 6/2006 | Ando et al. |

FOREIGN PATENT DOCUMENTS

| | | |
|---|---|---|
| WO | WO-2005/111627 A2 | 11/2005 |
| WO | WO-2007/025348 A1 | 3/2007 |
| WO | WO-2008/128221 A1 | 10/2008 |

OTHER PUBLICATIONS

Harvey, Mass Spectrometry Reviews, 18:349-451(1999). See in particular p. 417.*
Anumula, 2006, *Anal. Biochem.*, 350(1):1.
Bossio, et al., 2002, *Anal. Chemistry 20020401 US*, 74(7):1674-1679.
International Seach Report for PCT/US2008/060334 (Dec. 8, 2004).
Irungu, et al., 2006, *Anal. Chem.*, 78(4):1181-1190.
Jiang, et al., 2005, *J. Amer. Soc. Mass Spectrom.*, 16(3):340-348.
Klein, et al., 1992, *Carbohydr Res.*, 236:9-16.
Kuberan, et al., 2002, *J.Am. Soc.*, 124:8707-8718.

(Continued)

*Primary Examiner* — Jill Warden
*Assistant Examiner* — Monique Cole
(74) *Attorney, Agent, or Firm* — Choate Hall & Stewart LLP; Brenda Hershbach Jarrell

(57) ABSTRACT

The present disclosure provides, among other things, methods for the identification of sulfated glycans in a mixture of glycans.

20 Claims, 4 Drawing Sheets

Chemical Formula: $C_8H_{15}NO_6$
Exact Mass: 221.09
Molecular Weight: 221.21
m/z: 221.09 (100.0%), 222.09 (9.3%), 223.09 (1.3%)
Elemental Analysis: C, 43.44; H, 6.83; N, 6.33; O, 43.40

Chemical Formula: $C_8H_{14}NO_9S^-$
Exact Mass: 300.04
Molecular Weight: 300.26
m/z: 300.04 (100.0%), 301.04 (10.2%), 302.03 (4.5%), 302.04 (2.0%)
Elemental Analysis: C, 32.00; H, 4.70; N, 4.66; O, 47.96; S, 10.68

OTHER PUBLICATIONS

Robbe, et al., 2004, *Rapid Commun. in Mass Spectrometry* , 18(4):412-420.

Shi, et al., 1998, *Proc. Natl. Acad. Sci.*, 95:11532-11537.

Townsend, R.R., 1995, "Carbohydrate Analysis," Ed. Z. El Rassi, pp. 181-209.

Written Opinion for PCT/US2008/060334 (Dec. 8, 2004).

Zhang, et al., 2006, *Elsevier Science Inc.*, 17(9):1044-0305.

Pace, et al., "Characterization of Minor N-linked Glycans on Antibodies Using Endo H Release and MALDI-Mass Spectrometry," Analytical Letters, 42: 1711-1724, 2009.

* cited by examiner

Chemical Formula: $C_8H_{15}NO_6$
Exact Mass: 221.09
Molecular Weight: 221.21
m/z: 221.09 (100.0%), 222.09 (9.3%), 223.09 (1.3%)
Elemental Analysis: C, 43.44; H, 6.83; N, 6.33; O, 43.40

Chemical Formula: $C_8H_{14}NO_9S^-$
Exact Mass: 300.04
Molecular Weight: 300.26
m/z: 300.04 (100.0%), 301.04 (10.2%), 302.03 (4.5%), 302.04 (2.0%)
Elemental Analysis: C, 32.00; H, 4.70; N, 4.66; O, 47.96; S, 10.68

NeuAc1 Fuc1 Gal1 Man3 GlcNAc5 Sulfate2
Elemental Composition
C81O64N6H134S2
M = 100%
M+1 = 87%
M+2 = 91%
M+3 = 51%
M+4 = 30%
% Intensity
Mass (m/z)

= Sulfate
= NeuAc
= Galactose
= N-Acetylglucosamine
= Mannose
= Fucose
NeuAc1 Fuc1 Gal3 Man3 GlcNAc5
Elemental Composition
C93O68N6H154
M = 100
M+1 = 95%
M+2 = 75%
M+3 = 30%
M+4 = 15%
% Intensity
Mass (m/z)

MS METHODS TO EVALUATE GLYCANS

CROSS-REFERENCE TO RELATED APPLICATIONS

This Application claims the benefit under 35 U.S.C. 371 of International Application No.: PCT/US2008/060334, filed Apr. 15, 2008 (published PCT application No. WO 2008/128221 A1, on Oct. 23, 2008), which claims priority to U.S. provisional application Ser. No. 60/923,677, filed Apr. 16, 2007, the entire contents of each of which are incorporated herein by reference.

BACKGROUND

Sulfation is one of the most common modifications found on carbohydrate moieties of glycoproteins, and can play an important role in the biological function of a glycoprotein. For example, sulfated glycans are known to be involved in several biological recognition events such as lymphocyte homing and removal of pituitary hormones from circulation. Phosphorylation is another common modification on carbohydrates that can significantly affect the biological function of a glycoprotein. However, phosphate and sulfate groups have essentially the same mass (80 Da). As a result, it is often difficult to differentiate between sulfated and phosphorylated species. There is a need, therefore, for techniques that can detect sulfated and/or phosphorylated glycan species, and a particular need for techniques that can distinguish between the two.

SUMMARY

In various aspects, the present disclosure provides methods for the identification of sulfated glycans in a mixture of glycans. In some embodiments, methods described herein use the naturally occurring isotopic abundance distribution of sulfur, which contains an $S^{34}$:$S^{32}$ ratio of about 4.5%, to, e.g., facilitate identifying sulfated glycans, distinguish phosphorylated from sulfated glycans, and/or determine the amount of sulfation relative to one or more other post-translational modifications.

In certain embodiments, a sample comprising a mixture of glycans is subjected to mass analysis to generate a mass spectrum of at least a portion of the mixture. A mass spectrum comprises a list of mass signals (also referred to as mass peaks). Each mass signal has an associated strength (related to the abundance of the ion) and an associated mass (related to, e.g., the mass-to-charge (m/z) ratio of the ion).

Some methods compare the signal strength of an ion signal at [M] mass units to that at [M+2] mass units, for example, where the mass scale is given in atomic mass units (amu), the mass signal at M (amu) is compared to that at M+2 amu. Such a comparison of signal strengths can be repeated for a plurality of mass peak pairs. Mass peaks corresponding to sulfated glycans are identified based at least on the signal strength ratio between the [M] and [M+2] ions between similar carbohydrate species. Mass signal pairs ([M+2], [M]) of glycans containing higher [M+2]/[M] ratios are identified as sulfated glycans. In various embodiments, methods further confirm this assignment by subjecting a portion of the glycan mixture to analysis with a mass spectrometric technique having more than one analytical dimension, e.g, LC-MS, MS/MS, etc. In another preferred embodiment, the methods further confirm this assignment by comparing the isotopic distribution of the species to a theoretical mass spectra from a model glycan.

In various aspects, provided are methods for identifying sulfated glycans in a mixture of glycans, comprising steps of: (a) providing a mass spectrum for a mixture of glycans; (b) determining for multiple pairs of mass peaks in the mass spectrum separated by two mass units, [M] and [M+2], the signal strength ratio [M+2]/[M] for each pair; and (c) identifying a mass peak associated with a first glycan as that of a sulfated glycan when at least the [M+2]/[M] ratio associated with the first glycan is greater than the [M+2]/[M] ratio associated with mass peaks corresponding to one or more similar glycans by a selected threshold. In various embodiments, the selected threshold is where the [M+2]/[M] ratio of the first glycan relative to one or more other similar glycans is greater than about one or more of: (a) a factor of about 1.1; (b) a factor of about 1.2; (c) a factor of about 1.5; (d) a value of 0.02; and (e) a value of 0.04.

In various aspects, provided are methods for identifying sulfated glycans in a mixture of glycans, comprising steps of: (a) providing a mass spectrum for a mixture of glycans; (b) determining for multiple pairs of mass peaks in the mass spectrum separated by two mass units, [M] and [M+2], the signal strength ratio [M+2]/[M] for each pair; and (c) identifying a mass peak as arising from a sulfated glycan based at least on the distribution of [M+2]/[M] ratios for three or more similar glycans. In various embodiments, mass peaks that have [M+2]/[M] ratios in the higher value mode of a bimodal distribution of [M+2]/[M] ratios for three or more similar glycans are identified as arising from a sulfated glycan.

The signal strength of a mass signal can be determined, for example, from one or more of: (a) the maximum mass signal intensity over a given range of mass units; (b) the mean mass signal intensity over a given range of mass units; (c) the area associated with the mass peak given range of mass units; and (d) combinations of two or more thereof. The given range of mass units can be based on, for example, one or more of the full-width at half-maximum (FWHM) of a peak, the mass resolution of the mass spectrometer, etc.

In various embodiments of the present disclosure, a mass spectrum is first processed to remove electronic noise from, and/or to correct the baseline of, the mass spectrum before signal strengths are determined. Electronic noise removal and baseline correction can be accomplished by any suitable method known in the art. In various embodiments, signal strengths are corrected for variations in dynamic response, resolution, etc. of the mass spectrometer prior to comparison of signal strengths.

In various embodiments, methods use the difference in the natural isotopic abundance distribution between sulfur and phosphorus to differentiate sulfated from phosphorylated structures. For example, the natural isotopic abundance ratio of $S^{34}$:$S^{32}$ is about 4.5:100, or 4.5%, and thus, mass signals originating from sulfated glycans should produce a satellite peak at about [M+2] and an increased [M+2]/[M] ratio, whereas peaks associated with phosphorylated structures should show substantially no such correlation between [M] and [M+2] peak strengths.

The foregoing and other aspects, embodiments, and features of the present inventions can be more fully understood from the following description in conjunction with the accompanying drawing. The figures of the drawing are not necessarily to scale, emphasis instead being placed upon illustrating the principles of the disclosure.

DEFINITIONS

Figure 1A:
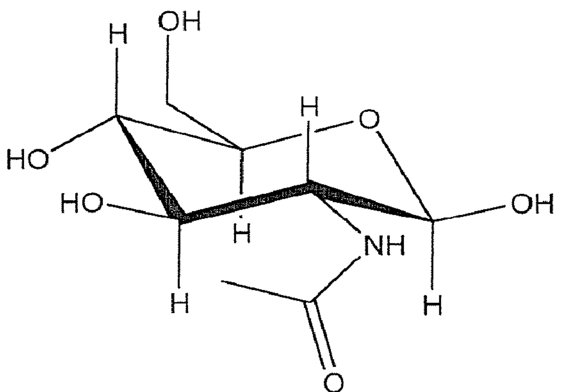
FIGS. 1A and 1B provide, respectively, schematic illustrations of model structures of N-Acetylglucosamine and N-Acetylglucosamime-6-sulfate to illustrate the difference in isotopic distribution due to the presence of the sulfate moiety.
Figure 1B:
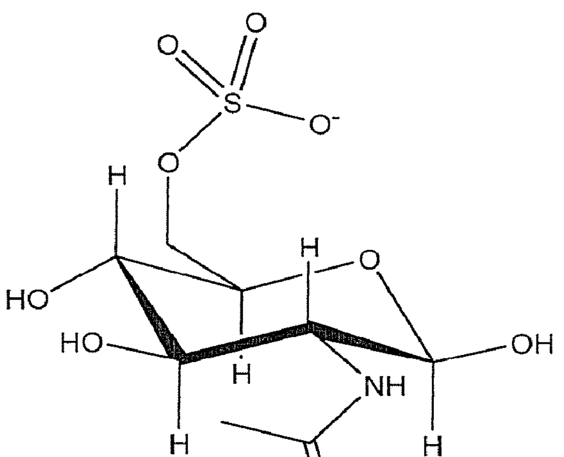

Approximately, About, Ca.: As used herein, the terms "approximately", "about" or "ca.," as applied to one or more values of interest, refer to a value that is similar to a stated reference value. In certain embodiments, the terms "approximately", "about" or "ca.," refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

Biological sample: The term "biological sample", as used herein, refers to any solid or fluid sample obtained from, excreted by or secreted by any living cell or organism, including, but not limited to, tissue culture, bioreactors, human or animal tissue, plants, fruits, vegetables, single-celled microorganisms (such as bacteria and yeasts) and multicellular organisms. For example, a biological sample can be a biological fluid obtained from, e.g., blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, e.g., a sample obtained from any organ or tissue (including a biopsy or autopsy specimen), can comprise cells (whether primary cells or cultured cells), medium conditioned by any cell, tissue or organ, tissue culture.

Cell-surface glycoprotein: As used herein, the term "cell-surface glycoprotein" refers to a glycoprotein, at least a portion of which is present on the exterior surface of a cell. In some embodiments, a cell-surface glycoprotein is a protein that is positioned on the cell surface such that at least one of the glycan structures is present on the exterior surface of the cell.

Cell-surface glycan: A "cell-surface glycan" is a glycan that is present on the exterior surface of a cell. In many embodiments of the present disclosure, a cell-surface glycan is covalently linked to a polypeptide as part of a cell-surface glycoprotein. A cell-surface glycan can also be linked to a cell membrane lipid.

Glycan: As is known in the art and used herein "glycans" are sugars. Glycans can be monomers or polymers of sugar residues, but typically contain at least three sugars, and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

Glycan preparation: The term "glycan preparation" as used herein refers to a set of glycans obtained according to a particular production method. In some embodiments, glycan preparation refers to a set of glycans obtained from a glycoprotein preparation (see definition of glycoprotein preparation below).

Glycoconjugate: The term "glycoconjugate", as used herein, encompasses all molecules in which at least one sugar moiety is covalently linked to at least one other moiety. The term specifically encompasses all biomolecules with covalently attached sugar moieties, including for example N-linked glycoproteins, O-linked glycoproteins, glycolipids, proteoglycans, etc.

Glycoform: The term "glycoform", is used herein to refer to a particular form of a glycoconjugate. That is, when the same backbone moiety (e.g., polypeptide, lipid, etc) that is part of a glycoconjugate has the potential to be linked to different glycans or sets of glycans, then each different version of the glycoconjugate (i.e., where the backbone is linked to a particular set of glycans) is referred to as a "glycoform".

Glycolipid: The term "glycolipid" as used herein refers to a lipid that contains one or more covalently linked sugar moieties (i.e., glycans). The sugar moiety(ies) may be in the form of monosaccharides, disaccharides, oligosaccharides, and/or polysaccharides. The sugar moiety(ies) may comprise a single unbranched chain of sugar residues or may be comprised of one or more branched chains. In certain embodiments, sugar moieties may include sulfate and/or phosphate groups. In certain embodiments, glycoproteins contain O-linked sugar moieties; in certain embodiments, glycoproteins contain N-linked sugar moieties.

Glycoprotein: As used herein, the term "glycoprotein" refers to a protein that contains a peptide backbone covalently linked to one or more sugar moieties (i.e., glycans). As is understood by those skilled in the art, the peptide backbone typically comprises a linear chain of amino acid residues. In certain embodiments, the peptide backbone spans the cell membrane, such that it comprises a transmembrane portion and an extracellular portion. In certain embodiments, a peptide backbone of a glycoprotein that spans the cell membrane comprises an intracellular portion, a transmembrane portion, and an extracellular portion. In certain embodiments, methods of the present disclosure comprise cleaving a cell surface glycoprotein with a protease to liberate the extracellular portion of the glycoprotein, or a portion thereof, wherein such exposure does not substantially rupture the cell membrane. The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments, sugar moieties may include sulfate and/or phosphate groups. Alternatively or additionally, sugar moieties may include acetyl, glycolyl, propyl or other alkyl modifications. In certain embodiments, glycoproteins contain O-linked sugar moieties; in certain embodiments, glycoproteins contain N-linked sugar moieties. In certain embodiments, methods disclosed herein comprise a step of analyzing any or all of cell surface glycoproteins, liberated fragments (e.g., glycopeptides) of cell surface glycoproteins, cell surface glycans attached to cell surface glycoproteins, peptide backbones of cell surface glycoproteins, fragments of such glycoproteins, glycans and/or peptide backbones, and combinations thereof.

Glycosidase: The term "glycosidase" as used herein refers to an agent that cleaves a covalent bond between sequential sugars in a glycan or between the sugar and the backbone moiety (e.g., between sugar and peptide backbone of glycoprotein). In some embodiments, a glycosidase is an enzyme. In certain embodiments, a glycosidase is a protein (e.g., a protein enzyme) comprising one or more polypeptide chains. In certain embodiments, a glycosidase is a chemical cleavage agent (e.g., hydrazine, sodium borohydride, trifluoromethanesulfonic acid, etc, and combinations thereof).

Glycosylation pattern: As used herein, the term "glycosylation pattern" refers to the set of glycan structures present on a particular sample. For example, a particular glycoconjugate (e.g., glycoprotein) or set of glycoconjugates (e.g., set of glycoproteins) will have a glycosylation pattern. In some embodiments, reference is made to the glycosylation pattern of cell surface glycans. A glycosylation pattern can be characterized by, for example, the identities of glycans, amounts (absolute or relative) of individual glycans or glycans of particular types, degree of occupancy of glycosylation sites, etc., or combinations of such parameters.

Glycoprotein preparation: A "glycoprotein preparation", as that term is used herein, refers to a set of individual glycoprotein molecules, each of which comprises a polypeptide having a particular amino acid sequence (which amino acid sequence includes at least one glycosylation site) and at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms.

N-glycan: The term "N-glycan," as used herein, refers to a polymer of sugars that has been released from a glycoconjugate but was formerly linked to the glycoconjugate via a nitrogen linkage (see definition of N-linked glycan below).

N-linked glycans: N-linked glycans are glycans that are linked to a glycoconjugate via a nitrogen linkage. A diverse assortment of N-linked glycans exists, but is typically based on the common core pentasaccharide $(Man)_3(GlcNAc)(GlcNAc)$.

O-glycan: The term "O-glycan," as used herein, refers to a polymer of sugars that has been released from a glycoconjugate but was formerly linked to the glycoconjugate via an oxygen linkage (see definition of O-linked glycan below).

O-linked glycans: O-linked glycans are glycans that are linked to a glycoconjugate via an oxygen linkage. O-linked glycans are typically attached to glycoproteins via N-acetyl-D-galactosamine (GalNAc) or via N-acetyl-D-glucosamine (GlcNAc) to the hydroxyl group of L-serine (Ser) or L-threonine (Thr). Some O-linked glycans also have modifications such as acetylation and sulfation. In some instances O-linked glycans are attached to glycoproteins via fucose or mannose to the hydroxyl group of L-serine (Ser) or L-threonine (Thr).

Phosphorylation: As used herein, the term "phosphorylation" refers to the process of covalently adding one or more phosphate groups to a molecule (e.g., to a glycan).

Protease: The term "protease" as used herein refers to an agent that cleaves a peptide bond between sequential amino acids in a polypeptide chain. In some embodiments, a protease is an enzyme (i.e., a proteolytic enzyme). In certain embodiments, a protease is a protein (e.g., a protein enzyme) comprising one or more polypeptide chains. In certain embodiments, a protease is a chemical cleavage agent.

Protein: In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

Sialic acid: The term "sialic acid," as used herein, is a generic term for the N- or O-substituted derivatives of neuraminic acid, a nine-carbon monosaccharide. The amino group of neuraminic acid typically bears either an acetyl or a glycolyl group in a sialic acid. The hydroxyl substituents present on the sialic acid may be modified by acetylation, methylation, sulfation, and phosphorylation. The predominant sialic acid is N-acetylneuraminic acid (Neu5Ac). Sialic acids impart a negative charge to glycans, because the carboxyl group tends to dissociate a proton at physiological pH. Exemplary deprotonated sialic acids are as follows:

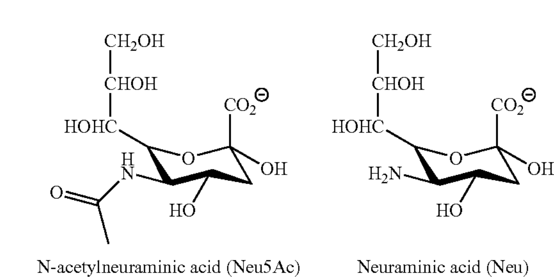

N-acetylneuraminic acid (Neu5Ac) Neuraminic acid (Neu)

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. To give but one particular example, when it is said that a treatment does not "substantially" rupture the cell membranes, it is meant to indicate that all or most of the cell membranes remain intact during and after the treatment, for example so that intracellular glycoproteins or glycopeptides are thus not released from the cells. In certain embodiments, the term "substantially", as applied to unruptured cell membranes, refers to condition wherein 15%, 10%, 9%, 8%, 7%, 6%, 5%, 4%, 3%, 2%, 1%, or fewer of the cells subjected to a particular treatment exhibit measurable ruptured cell membranes. In certain embodiments, the term "substantially", as applied to unruptured cell membranes, refers to condition wherein none of the cells subjected to a particular treatment exhibit measurable ruptured cell membranes.

DETAILED DESCRIPTION OF CERTAIN EMBODIMENTS

In various aspects, the present disclosure provides methods for the identification of sulfated glycans in a mixture of glycans. In various embodiments, methods of the present disclosure can be used to facilitate the identification of sulfated carbohydrates in a complex mixture of carbohydrates. In various embodiments, methods can provide quantification of sulfated glycans and/or carbohydrates.

In various aspects, methods of the present disclosure can be applied to mixtures of glycans comprising glycans free in solution, glycans cleaved (e.g., enzymatic, chemical, etc.) from a peptide, protein, lipid etc., glycans on a protein, peptide, lipid, etc., and/or mixtures comprising combinations thereof.

Methods of the present inventions can be applied to many areas. For example, in various embodiments, provided are methods for differentiating sulfated glycans from phosphorylated glycans.

In various embodiments, methods comprise the steps of: subjecting a sample comprising a mixture of glycans to mass analysis to generate a mass spectrum of at least a portion of the mixture; comparing the signal strength of an ion signal at [M] mass units to that at [M+2] mass units; repeating the comparison for a plurality of different [M] and [M+2] pairs; and identifying as sulfated glycans those that have an increased [M+2]/[M] ratio relative to one or more other similar glycans.

In various embodiments, a glycan is identified as a sulfated glycan when its [M+2]/[M] ratio relative to one or more other similar glycans is greater than about one or more of: (a) a factor of about 1.1; (b) a factor of about 1.2; (c) a factor of about 1.5; (d) a value of 0.02; and (e) a value of 0.04. For example, consider a glycan of nominal mass $M_1$ with the signal strength ratio $[M_1+2]=Y$ and a similar glycan with nominal mass $M_c$ with the signal strength ratio $[M_c+2]/[M_c]=Z$, in various embodiments the glycan $M_1$ is identified as a sulfated glycan when one or more of: (a) Y/Z is greater than about 1.1; (b) Y/Z is greater than about 1.2; (c) Y/Z is greater than about 1.5; (d) Y is greater than about Z+0.2; and (e) Y is greater than about Z+0.4.

In various embodiments, a glycan is identified as a sulfated glycan when its [M+2]/[M] ratio relative to two or more other similar glycans is greater than the [M+2]/[M] ratio of other similar glycans by more than one standard deviation. In various embodiments, sulfated glycans are distinguished from unsulfated glycans of similar structure by the presence of a bimodal distribution in [M+2]/[M] values, the mass signals associated with the higher value mode of the distribution being identified as sulfated glycans.

Figure 2A:
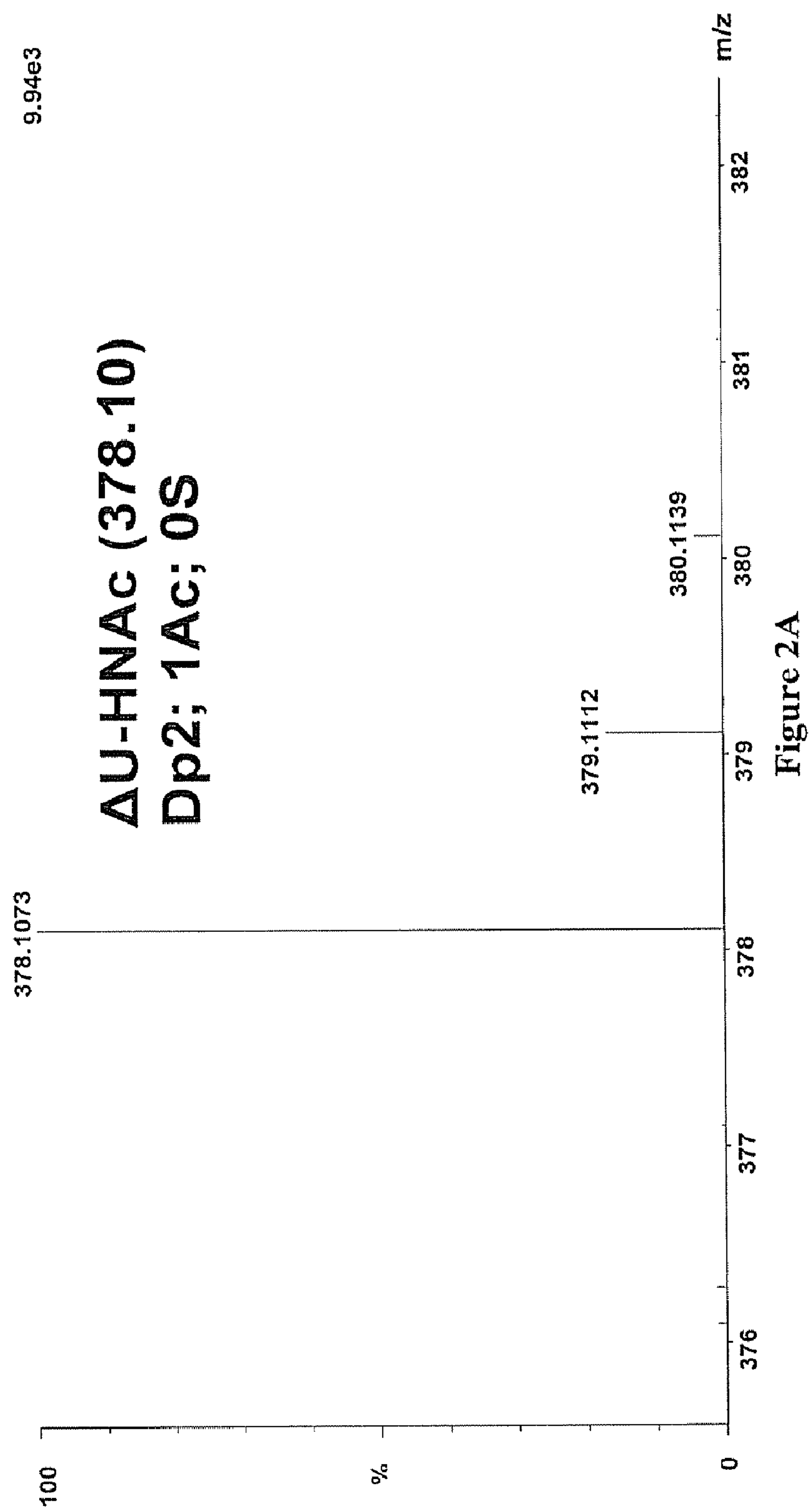
FIGS. 2A and 2B are mass spectra comparing the isotopic distribution between unsulfated ΔU-HNAC disaccharide, FIG. 2A, and a sulfated ΔU-HNAC6S disaccharide, FIG. 2B.
Figure 2B:
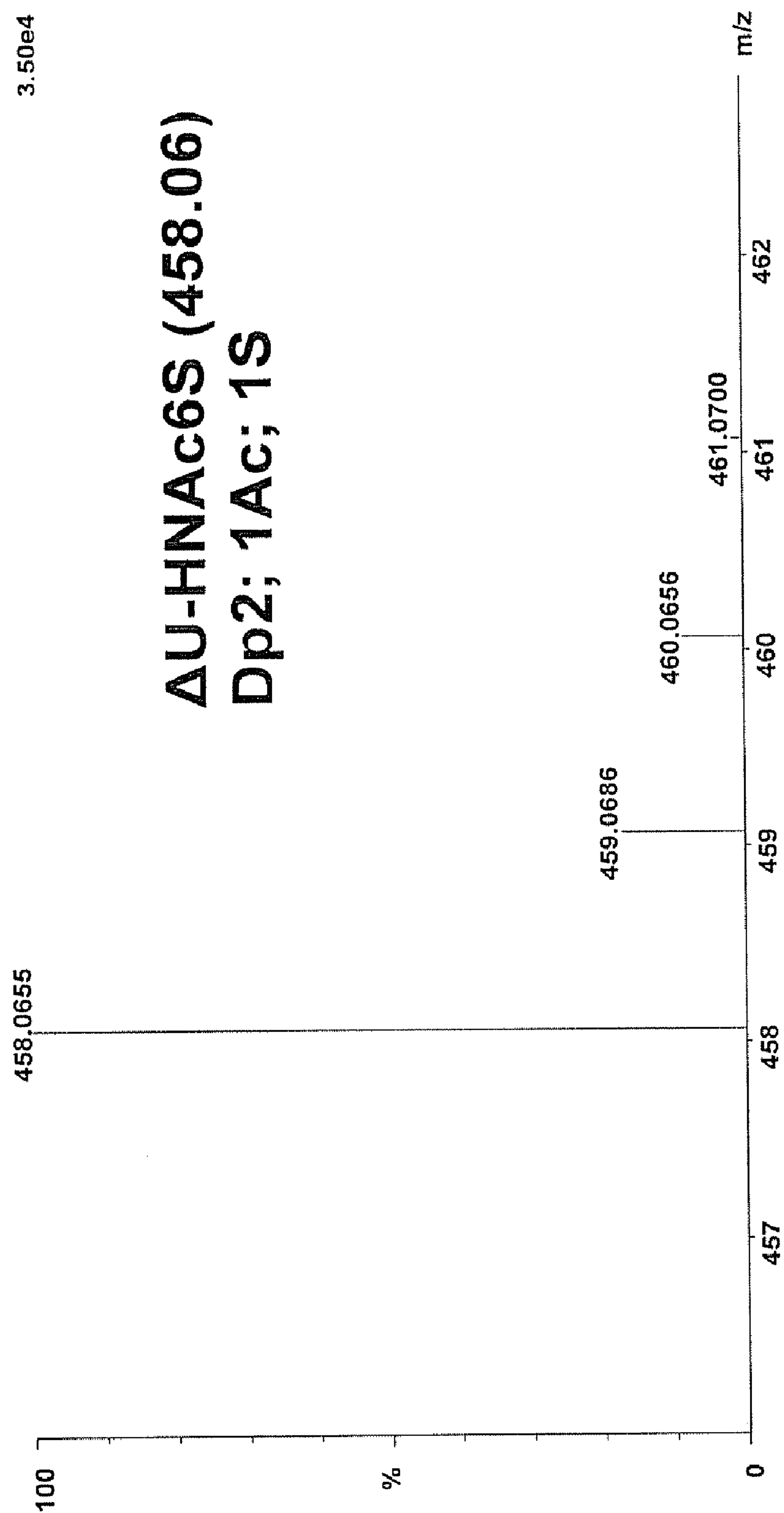

FIGS. 2A-B and 3A-B, illustrate examples of the identification of sulfated glycans by comparing the [M+2]/[M] ratios of similar glycans. In FIGS. 2A-B mass spectra, presented in an intensity only format, for unsulfated ΔU-HVAC disaccharide, FIG. 2A, and sulfated ΔU-HNAC6S disaccharide, FIG. 2B. The [M+2]/[M] ratio of the sulfated glycan was about 0.089 (or 8.9%) compared to that of a similar unsulfated glycan, which was about 0.04 (4%). In FIGS. 2A-B the sulfated glycan [M+2]/[M] ratio is both greater than the unsulfated [M+2]/[M] ratio by about 0.04 and by a factor of greater than about 1.5.

Figures 3A, 3B:
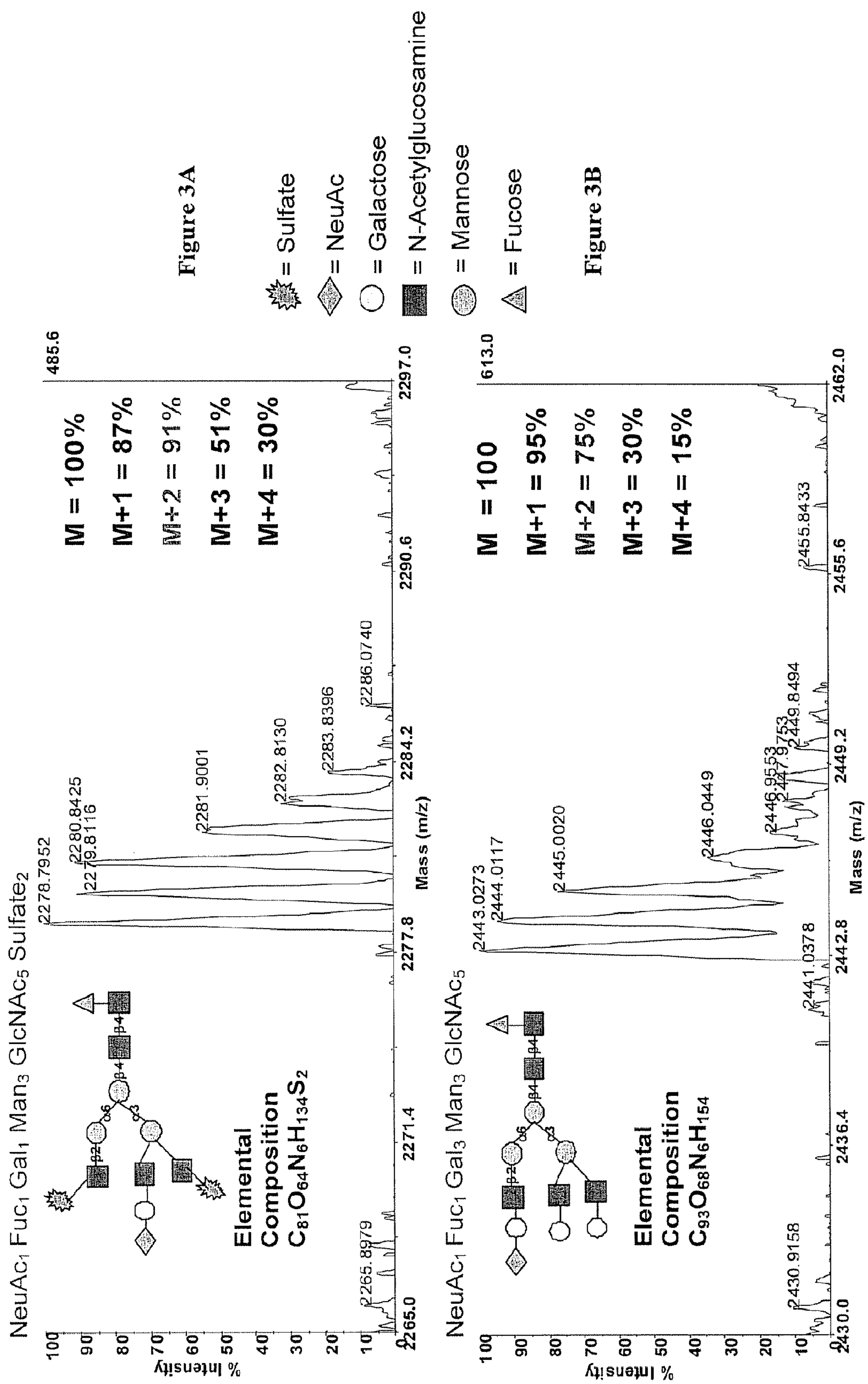
FIGS. 3A and 3B provide mass spectra and compare the isotopic distribution between a sulfated $NeuAc_1Fuc_1Gal_1Man_3GlcNAc_5Sulfate_2$ complex N-glycan, FIG. 3A, and an unsulfated $NeuAc_1Fuc_1Gal_3Man_3GlcNAc_5$ complex N-linked glycan, FIG. 3B.

In FIGS. 3A-B mass spectra are presented for two glycans of similar structure, a sulfated glycan ($NeuAc_1Fuc_1Gal_1Man_3GlcNAc_5Sulfate_2$ complex N-glycan), FIG. 3A, and an unsulfated glycan ($NeuAc_1Fuc_1Gal_3Man_3$ $GlcNAc_5$ complex N-linked glycan), FIG. 3B. The [M+2]/[M] ratio of the sulfated glycan was about 0.091 (or 91%) and that of a similar unsulfated glycan was about 0.75 (75%). In FIGS. 3A-B the sulfated glycan [M+2]/[M] ratio is both greater than the unsulfated [M+2]/[M] ratio by about 0.16 and by a factor of greater than about 1.2.

It is to be understood that although the relative strengths of a mass signal at [M] and [M+2] are discussed in terms of the ratio [M+2]/[M] that the ratio of [M]/[M+2] can be used as well with the realization that sulfated glycans are identified with lower ratios. It is also to be understood that the raw data used to construct a mass spectrum does not need to take the form of signal versus mass but can take the form of a signal versus some other parameter. For example, in a time-of-flight (TOF) mass spectrometer raw data are obtained as signal versus the flight time of the ions to a detector. Flight time is then related to the ion mass by a calibration function, e.g., the flight time is a linear function of the square root of the ion mass. In a Fourier transform ion cyclotron resonance (FTICR) mass spectrometer, the raw data obtained is essentially in the form of signal intensity versus cyclotron frequency and the frequency is then related to ion mass by a calibration function.

In various embodiments, potential glycan structures are predicted for one or more mass signals associated with a glycan and the predicted structures compared to determine which mass signals may arise from similar glycans and used to determine which mass signals [M+2]/[M] ratios are compared. For example, the family group of the predicted glycans can be compared to ascertain the degree of similarity.

In various embodiments, two glycans are similar when they are from the same glycan family. In various embodiments, two glycans are similar when the masses of the glycans are within ±20% (e.g., within ±15%, ±10%, ±5%) of each other. In various preferred embodiments, two glycans are similar when they are from the same glycan family and the masses of the glycans are within ±20% (e.g., within ±15%, ±10%, ±5%) of each other.

Examples of glycan families include, but are not limited to, (a) monosaccharides, (b) polysaccharides, (c) branched glycans, (d) linear glycans, (e) N-linked glycans, (f) O-linked glycans, etc. Examples of various N-linked glycan families include, but are not limited to, (a) the A2 family (disialylated, biantennary N-linked oligosaccharides; including A1 glycans (monosialylated, biantennary N-linked oligosaccharide), NA2 glycans (asialo-biantennary N-linked oligosaccharide); NGA2 glycans (asialo-, agalacto-biantennary N-linked oligosaccharide); M3N2 glycans, etc.); (b) the A2F family (disialylated, biantennary N-linked oligosaccharide with core fucose; including A1F glycans (monosialylated, biantennary N-linked oligosaccharide with core fucose), NA2F glycans (asialo-biantennary N-linked oligosaccharide with core fucose) NGA2F glycans (asialo-, agalacto-biantennary N-linked oligosaccharide with core fucose), etc.); (c) the A3 family (e.g., glycans fully sialylated on the non-reducing terminal galactosyl residues but differing in the distribution of a2,3 and a2,6 linked sialyl residues and the linkage one of the galactoses; including NA3 (asialo tri-antennary N-linked oligosaccharide derived from an A3 glycan) and NGA3 glycans (agalacto-triantennary N-linked oligosaccharide derived from an NA3 glycan), etc.); (d) the A4 family (glycans derived from tetra-antennary N-linked oligosaccharides; including NA4 glycans (asialo-tetraantennary N-linked oligosaccharide); NGA4 glycans (asialo-, agalacto-tetraantennary N-linked oligosaccharide derived from NA4 glycans); etc.); and (e) oligmannose family glycans (e.g., Man-5, Man-6, Man-7, Man-8, Man-9, etc. glycans).

For example, compares the FIGS. 3A and B mass spectra of two similar A3 glycans, $NeuAc_1Fuc_1Gal_1Man_3GlcNAc_5Sulfate_2$ complex N-glycan, FIG. 3A, and $NeuAc_1Fuc_1Gal_3Man_3GlcNAc_5$ complex N-linked glycan, FIG. 3B. As indicated by insets in FIGS. 3A and B, both glycans share an A3 structure, and more specifically an NGA3F family structure. In addition, the two glycans depicted and have masses within about 7% of each other.

In various embodiments, methods comprise subjecting a portion of a glycan mixture to analysis with a mass spectrometric technique where the mass peaks identified as arising from a sulfated glycan are subject to more than one analytical dimension to determine the presence of sulfur. In various embodiments, mass peaks identified as arising from a sulfated glycan are subject to MS/MS analysis, e.g., employing collision induced dissociation (CID) to determine the presence of sulfur.

Methods of the present inventions can be performed with a wide variety of mass spectrometry instruments and techniques, including but not limited to, MALDI-TOF-MS, MALDI-TOF-TOF-MS, LC-MS, LC-MS/MS, by direct infusion ESI-MS, etc. The use of a high resolution mass spectrometer, e.g., resolution of better than about 1 amu, is preferred.

A wide variety of techniques can be used to ionize molecules in the glycan mixture for analysis, including, but not limited to matrix-assisted laser/desorption ionization (MALDI) and electrospray ionization (ESI). It is typically preferred that the ionization source and conditions are chosen to substantially prevent the cleavage of the sulfates groups in the mass spectrometer source.

Methods of the present disclosure can be applied to glycans obtained from a wide variety of sources including, but not limited to, therapeutic formulations and biological samples. As used herein, the term "biological sample" refers to any solid or fluid sample obtained from, excreted by or secreted by any living cell or organism, including, but not limited to, tissue culture, human or animal tissue, plants, fruits, vegetables, single-celled microorganisms (such as bacteria and yeasts) and multicellular organisms. For example, a biological sample can be a biological fluid obtained from, e.g., blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, e.g., a sample obtained from any organ or tissue (including a biopsy or autopsy specimen), can comprise cells (whether primary cells or cultured cells), medium conditioned by any cell, tissue or organ, tissue culture.

In various embodiments, methods facilitate detecting sulfated glycan structures present in a mixture at low levels. For example, in various embodiments, sulfated glycan structures can be detected that are present in the low femtomole (fmol) range.

In various embodiments, methods of the present disclosure can be used to extend the dynamic range of a mass spectrometric technique for the detection of sulfated glycans. For example, in various embodiments, methods can be used to detect the presence of one or more undesired products or contaminants in a pharmaceutical or therapeutic present at concentrations four orders of magnitude lower than the overall glycan concentration in the sample. In various embodiments, methods can be used to monitor a pharmaceutical or therapeutic preparation process to detect undesired sulfated glycans at low concentrations, e.g., before they contaminate the pharmaceutical or therapeutic. In various embodiments the methods can be used to detect biomarkers indicative of, e.g., a disease state, prior to the appearance of symptoms and/or progression of the disease state to an untreatable or less treatable condition, by detecting one or more specific sulfated glycans and/or the change in the concentration of such glycans over time.

Applications

It will be appreciated that the techniques described herein can be utilized in any of a variety of applications. In general, these techniques are useful in any application that involves the structural characterization of sulfated glycans, particularly where it is desirable to distinguish sulfated glycans from other glycans.

Methods of the present disclosure can be applied to glycans obtained from a wide variety of sources including, but not limited to, therapeutic formulations and biological samples. A biological sample may undergo one or more analysis and/or purification steps prior to or after being analyzed according to the present disclosure. To give but a few examples, in some embodiments, a biological sample is treated with one or more proteases and/or glycosidases (e.g., so that glycans are released); in some embodiments, glycans in a biological sample are labeled with one or more detectable markers or other agents that may facilitate analysis by, for example, mass spectrometry or NMR. Any of a variety of separation and/or isolation steps may be applied to a biological sample in accordance with the present disclosure.

Methods of the present disclosure can be utilized to analyze glycans in any of a variety of states including, for instance, free glycans, glycoconjugates (e.g., glycopeptides, glycolipids, proteoglycans, etc.), cell-associated glycans (e.g., nucleus-, cytoplasm-, cell-membrane-associated glycans, etc.); glycans associated with cellular, extracellular, intracellular, and/or subcellular components (e.g., proteins); glycans in extracellular space (e.g., cell culture medium), etc.

Methods of the present disclosure may be used in one or more stages of process development for the production of a therapeutic or other commercially relevant glycoprotein of interest. Non-limiting examples of such process development stages that can employ methods of the present disclosure include cell selection, clonal selection, media optimization, culture conditions, process conditions, and/or purification procedure. Those of ordinary skill in the art will be aware of other process development stages.

The present disclosure can also be utilized to monitor the extent and/or type of glycosylation occurring in a particular cell culture, thereby allowing adjustment or possibly termination of the culture in order, for example, to achieve a particular desired glycosylation pattern or to avoid development of a particular undesired glycosylation pattern.

The present disclosure can also be utilized to assess glycosylation characteristics of cells or cell lines that are being considered for production of a particular desired glycoprotein (for example, even before the cells or cell lines have been engineered to produce the glycoprotein, or to produce the glycoprotein at a commercially relevant level).

For example, where the target glycoprotein is a therapeutic glycoprotein, for example having undergone regulatory review in one or more countries, it will often be desirable to monitor cultures to assess the likelihood that they will generate a product with a glycosylation pattern as close to the established glycosylation pattern of the pharmaceutical product as possible, whether or not it is being produced by exactly the same route. As used herein, "close" refers to a glycosylation pattern having at least about a 75%, 80%, 85%, 90%, 95%, 98%, or 99% correlation to the established glycosylation pattern of the pharmaceutical product. In such embodiments, samples of the production culture are typically taken at multiple time points and are compared with an established standard or with a control culture in order to assess relative glycosylation.

In some embodiments of the present disclosure, a desired glycosylation pattern will be more extensive. For example, in some embodiments, a desired glycosylation pattern shows high (e.g., greater than about 60%, about 65%, about 70%, about 75%, about 80%, about 85%, about 90%, about 95%, about 98%, about 99%, or more) occupancy of glycosylation sites; in some embodiments, a desired glycosylation pattern shows, a high degree of branching (e.g., greater than about 60%, about 65%, about 70%, about 75%, about 80%, about 85%, about 90%, about 95%, about 98%, about 99% or more have tri or tetra-antennary structures).

In some embodiments of the present disclosure, a desired glycosylation pattern will be less extensive. For example, in some embodiments, a desired cell surface glycosylation pattern shows low (e.g., less than about 50%, about 45%, about 40%, about 35%, about 30%, about 25%, about 20%, about 15%, about 15%, about 5%, about 1%, or less) occupancy of glycosylation sites; and/or a low degree of branching (e.g., less than about 20%, about 15%, about 10%, about 5%, about 1% or less have tri or tetra-antennary structures).

In some embodiments, a desired glycosylation pattern will be more extensive in some aspects and less extensive in others. For example, it may be desirable to employ a cell line that tends to produce glycoproteins with long, unbranched oligosaccharide chains. Alternatively, it may be desirable employ a cell line that tends to produce glycoproteins with short, highly branched oligosaccharide chains.

In some embodiments, a desired glycosylation pattern will be enriched for a particular type of glycan structure. For example, in some embodiments, a desired glycosylation pattern will have low levels (e.g., less than about 20%, about 15%, about 10%, about 5%, about 1%, or less) of high mannose or hybrid structures, high levels (e.g., greater than about 60%, about 65%, about 70%, about 75%, about 80%, about 85%, about 90%, about 95%, about 98%, about 99%, or more) of high mannose structures, high levels (e.g., greater than about 60%, about 65%, about 70%, about 75%, about 80%, about 85%, about 90%, about 95%, about 98%, about 99%, or more; for example at least one per glycoprotein) phosphorylated high mannose, or low levels (e.g., less than about 20%, about 15%, about 10%, about 5%, about 1%, or less) of phosphorylated high mannose.

In some embodiments, a desired glycosylation pattern will include at least about one sialic acid. In some embodiments, a desired glycosylation pattern will include a high level (e.g., greater than about 60%, about 65%, about 70%, about 75%, about 80%, about 85%, about 90%, about 95%, about 98%, about 99%, or more) of termini that are sialylated. In some embodiments, a desired glycosylation pattern that includes sialyation will show at least about 85%, about 90%, about 95%, about 98%, about 99%, or more N-acetylneuraminic acid and/or less than about 20%, about 15%, about 10%, about 5%, about 1%, or less N-glycolylneuraminic acid.

In some embodiments, a desired glycosylation pattern shows specificity of branch elongation (e.g., greater than about 60%, about 65%, about 70%, about 75%, about 80%, about 85%, about 90%, about 95%, about 98%, about 99%, or more of extension is on α1,6 mannose branches; or greater than about 60%, about 65%, about 70%, about 75%, about 80%, about 85%, about 90%, about 95%, about 98%, about 99%, or more of extension is on α1,3 mannose branches).

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of core fucosylation.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a sulfated glycan.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a phosphorylated glycan.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a sialic acid linked to an N-acetylglucosamine.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of an acetylated glycan.

Whether or not monitoring production of a particular target protein for quality control purposes, the present disclosure may be utilized, for example, to monitor glycosylation at particular stages of development, or under particular growth conditions.

In some particular embodiments, methods described herein can be used to characterize and/or control or compare the quality of therapeutic products. To give but one example, the present methodologies can be used to assess glycosylation in cells producing a therapeutic protein product. Particularly given that glycosylation can often affect the activity, bioavailability, or other characteristics of a therapeutic protein product, methods for assessing cellular glycosylation during production of such a therapeutic protein product are particularly desirable. Among other things, the present disclosure can facilitate real time analysis of glycosylation in production systems for therapeutic proteins.

Representative therapeutic glycoprotein products whose production and/or quality can be monitored in accordance with the present disclosure include, for example, any of a variety of hematologic agents (including, for instance, erythropoietins, blood-clotting factors, etc.), interferons, colony stimulating factors, antibodies, enzymes, and hormones.

Representative commercially available glycoprotein products include, for example:

| Protein Product | Reference Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |

-continued

| Protein Product | Reference Drug |
|---|---|
| laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| bivalirudin | Angiomax ® |
| darbepoetin alfa | Aranesp ™ |
| bevacizumab | Avastin ™ |
| interferon beta-1a; recombinant | Avonex ® |
| coagulation factor IX | BeneFix ™ |
| Interferon beta-1b | Betaseron ® |
| Tositumomab | Bexxar ® |
| antihemophilic factor | Bioclate ™ |
| human growth hormone | BioTropin ™ |
| botulinum toxin type A | Botox ® |
| alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune Fab, ovine | DigiFab ™ |
| rasburicase | Elitek ® |
| etanercept | Enbrel ® |
| epoietin alfa | Epogen ® |
| cetuximab | Erbitux ™ |
| algasidase beta | Fabrazyme ® |
| urofollitropin | Fertinex ™ |
| follitropin beta | Follistim ™ |
| teriparatide | Forteo ® |
| human somatropin | GenoTropin ® |
| glucagon | GlucaGen ® |
| follitropin alfa | Gonal-F ® |
| antihemophilic factor | Helixate ® |
| Antihemophilic Factor; Factor XIII | Hemofil ® |
| insulin | Humalog ® |
| antihemophilic factor/von Willebrand factor complex-human | Humate-P ® |
| somatotropin | Humatrope ® |
| adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| palifermin | Kepivance |
| anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa, for injection | Luveris |
| OspA lipoprotein | LYMErix ™ |
| ranibizumab | Lucentis ® |
| gemtuzumab ozogamicin | Mylotarg ™ |
| galsulfase | Naglazyme ™ |
| nesiritide | Natrecor ® |
| pegfilgrastim | Neulasta ™ |
| oprelvekin | Neumega ® |
| filgrastim | Neupogen ® |
| fanolesomab | NeutroSpec ™ (formerly LeuTech ®) |
| somatropin [rDNA] | Norditropin ®/Norditropin Nordiflex ® |
| insulin; zinc suspension; | Novolin L ® |
| insulin; isophane suspension | Novolin N ® |
| insulin, regular; | Novolin R ® |
| insulin | Novolin ® |
| coagulation factor VIIa | NovoSeven ® |
| somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| human chorionic gonadotropin | Ovidrel ® |
| peginterferon alfa-2a | Pegasys ® |

-continued

| Protein Product | Reference Drug |
|---|---|
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| aldesleukin | Proleukin, IL-2 ® |
| somatrem | Protropin ® |
| dornase alfa | Pulmozyme ® |
| Efalizumab; selective, reversible T-cell blocker | Raptiva ™ |
| combination of ribavirin and alpha interferon | Rebetron ™ |
| Interferon beta 1a | Rebif ® |
| antihemophilic factor | Recombinate ® |
| rAHF/ntihemophilic factor | ReFacto ® |
| lepirudin | Refludan ® |
| infliximab | Remicade ® |
| abciximab | ReoPro ™ |
| reteplase | Retavase ™ |
| rituximab | Rituxan ™ |
| interferon alfa-2a | Roferon-A ® |
| somatropin | Saizen ® |
| synthetic porcine secretin | SecreFlo ™ |
| basiliximab | Simulect ® |
| eculizumab | Soliris ® |
| pegvisomant | Somavert ® |
| Palivizumab; recombinantly produced, humanized mAb | Synagis ™ |
| thyrotropin alfa | Thyrogen ® |
| tenecteplase | TNKase ™ |
| natalizumab | Tysabri ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| daclizumab | Zenapax ® |
| ibritumomab tiuxetan | Zevalin ™ |
| Somatotropin | Zorbtive ™ (Serostim ®) |

In some embodiments, the disclosure provides methods in which glycans from different sources or samples are compared with one another. In some such examples, multiple samples from the same source are obtained over time, so that changes in glycosylation patterns (and particularly in cell surface glycosylation patterns) are monitored. In some embodiments, one of the samples is a historical sample or a record of a historical sample.

In some embodiments, glycans from different cell culture samples prepared under conditions that differ in one or more selected parameters (e.g., cell type, culture type [e.g., continuous feed vs batch feed, etc.], culture conditions [e.g., type of media, presence or concentration of particular component of particular medium (a), osmolarity, pH, temperature, timing or degree of shift in one or more components such as osmolarity, pH, temperature, etc.], culture time, isolation steps, etc.) but are otherwise identical, are compared, so that effects of the selected parameter on N-glycosylation patterns are determined. In certain embodiments, glycans from different cell culture samples prepared under conditions that differ in a single selected parameter are compared so that effects of the single selected parameter on glycosylation patterns is determined. Among other applications, therefore, use of techniques as described herein may facilitate determination of the effects of particular parameters on glycosylation patterns in cells.

In some embodiments, glycans from different batches of a glycoprotein of interest (e.g., a therapeutic glycoprotein), whether prepared by the same method or by different methods, and whether prepared simultaneously or separately, are compared. In such embodiments, the present disclosure facilitates quality control of glycoprotein preparation. Alternatively or additionally, some such embodiments facilitate monitoring of progress of a particular culture producing a glycoprotein of interest (e.g., when samples are removed from the culture at different time points and are analyzed and compared to one another). In some examples, multiple samples from the same source are obtained over time, so that changes in glycosylation patterns are monitored. In some embodiments, glycan-containing samples are removed at about 30 second, about 1 minute, about 2 minute, about 5 minute, about 10 minute, about 30 minute, about 1 hour, about 2 hour, about 3 hour, about 4 hour, about 5 hour, about 10 hour, about 12 hour, or about 18 hour intervals, or at even longer intervals. In some embodiments, glycan-containing samples are removed at irregular intervals. In some embodiments, glycan-containing samples are removed at 5 hour intervals.

Methods of the present disclosure may be used in one or more stages of process development for the production of a therapeutic or other commercially relevant glycoprotein of interest. Non-limiting examples of such process development stages that can employ methods of the present disclosure include cell selection, clonal selection, media optimization, culture conditions, process conditions, and/or purification procedure. Those of ordinary skill in the art will be aware of other process development stages.

In any of these embodiments, features of the glycan analysis can be recorded, for example in a quality control record. As indicated above, in some embodiments, a comparison is with a historical record of a prior, or standard batch and/or with a reference sample of glycoprotein.

In certain embodiments, the present disclosure may be utilized in studies to modify the glycosylation characteristics of a cell, for example to establish a cell line and/or culture conditions with one or more desirable glycosylation characteristics. Such a cell line and/or culture conditions can then be utilized, if desired, for production of a particular target glycoconjugate (e.g., glycoprotein) for which such glycosylation characteristic(s) is/are expected to be beneficial.

In certain embodiments, techniques of the present disclosure are applied to glycans that are present on the surface of cells. In some such embodiments, the analyzed glycans are substantially free of non-cell-surface glycans. In some such embodiments, the analyzed glycans, when present on the cell surface, are present in the context of one or more cell surface glycoconjugates (e.g., glycoproteins or glycolipids).

In some particular embodiments, cell surface glycans are analyzed in order to assess glycosylation of one or more target glycoproteins of interest, particularly where such target glycoproteins are not cell surface glycoproteins. Such embodiments can allow one to monitor glycosylation of a target glycoprotein without isolating the glycoprotein itself. In certain embodiments, the present disclosure provides methods of using cell-surface glycans as a readout of or proxy for glycan structures on an expressed glycoprotein of interest. In certain embodiments, such methods include, but are not limited to, post process, batch, screening or "in line" measurements of product quality. Such methods can provide for an independent measure of the glycosylation pattern of a produced glycoprotein of interest using a byproduct of the production reaction (e.g., the cells) without requiring the use of destruction of any produced glycoprotein. Furthermore, methods of the present disclosure can avoid the effort required for isolation of product and the potential selection of product glycoforms that may occur during isolation.

In certain embodiments, techniques of the present disclosure are applied to glycans that are secreted from cells. In some such embodiments, the analyzed glycans are produced by cells in the context of a glycoconjugate (e.g., a glycoprotein or glycolipid).

According to the present disclosure, techniques described herein can be used to detect desirable or undesirable glycans, for example to detect or quantify the presence of one or more contaminants in a product, or to detect or quantify the presence of one or more active or desired species.

In various embodiments the methods can be used to detect biomarkers indicative of, e.g., a disease state, prior to the appearance of symptoms and/or progression of the disease state to an untreatable or less treatable condition, by detecting one or more specific glycans whose presence or level (whether absolute or relative) may be correlated with a particular disease state (including susceptibility to a particular disease) and/or the change in the concentration of such glycans over time.

In certain embodiments, methods described herein facilitate detection of glycans that are present at very low levels in a source (e.g., a biological sample, glycan preparation, etc.). In such embodiments, it is possible to detect and/or optionally quantify the levels of glycans that are present at levels less than about 10%, 5%, 4%, 3%, 2%, 1.5%, 1%, 0.75%, 0.5%, 0.25%, 0.1%, 0.075%, 0.05%, 0.025%, or 0.01% within a population of glycans. In some embodiments, it is possible to detect and/or optionally quantify the levels of glycans comprising between 0.1% and 5%, e.g., between 0.1% and 2%, e.g., between 0.1% and 1% of a glycan preparation. In certain embodiments, it is possible to detect and/or optionally quantify the levels of cell surface glycans at between about 0.1 fmol to about 1 mmol.

In some embodiments, methods described herein allow for detection of particular linkages that are present at low levels within a population of glycans. For example, the present methods allow for detection of particular linkages that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of glycans.

In some embodiments, methods described herein allow for detection of relative levels of individual glycan species within a population of glycans. For example, the area under each peak of a liquid chromatograph can be measured and expressed as a percentage of the total. Such an analysis provides a relative percent amount of each glycan species within a population of glycans.

In some embodiments, techniques described herein may be combined with one or more other technologies for the detection, analysis, and or isolation of glycans or glycoconjugates. For example, in certain embodiments, glycans are analyzed in accordance with the present disclosure using one or more available methods (to give but a few examples, see Anumula, *Anal. Biochem.* 350(1):1, 2006; Klein et al., *Anal. Biochem.*, 179:162, 1989; and/or Townsend, R. R. Carbohydrate Analysis" High Performance Liquid Chromatography and Capillary Electrophoresis., Ed. Z. El Rassi, pp 181-209, 1995, each of which is incorporated herein by reference in its entirety). For example, in some embodiments, glycans are characterized using one or more of chromatographic methods, electrophoretic methods, nuclear magnetic resonance methods, and combinations thereof. Exemplary such methods include, for example, NMR, mass spectrometry, liquid chromatography, 2-dimensional chromatography, SDS-PAGE, antibody staining, lectin staining, monosaccharide quantitation, capillary electrophoresis, fluorophore-assisted carbohydrate electrophoresis (FACE), micellar electrokinetic chromatography (MEKC), exoglycosidase or endoglycosidase treatments, and combinations thereof. Those of ordinary skill in the art will be aware of other methods that can be used to characterize glycans together with the IMAC methods described herein.

In some embodiments, glycan structure and composition can be analyzed by chromatographic methods, including but not limited to, liquid chromatography (LC), high performance liquid chromatography (HPLC), ultra performance liquid chromatography (HPLC), thin layer chromatography (TLC), amide column chromatography, and combinations thereof.

In some embodiments, glycan structure and composition can be analyzed by mass spectrometry (MS) and related methods, including but not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof.

In some embodiments, glycan structure and composition can be analyzed by electrophoretic methods, including but not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof.

In some embodiments, glycan structure and composition can be analyzed by nuclear magnetic resonance (NMR) and related methods, including but not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

EXAMPLES

Example 1

Identification of a Sulfated Glycan in a Mixture

In various embodiments, the methods of the present disclosure can be applied to mixtures of glycans. For example, a mixture of glycans is prepared for ESI using a methanol:water carrier solvent which may contain a suitable buffer, acid etc. The glycan mixture is then fed to the ESI-MS device (e.g., a MDS Sciex/Applied Biosystems API-III or API QSTAR™ instrument, a ThermoFinnigan LCQ™ Classic instrument, etc., operated in positive ion mode) in a substantially continuous fashion, such as via liquid chromatography or low injection with a mass calibration standard. The mass spectra generated is deconvoluted for multiple charging and the deconvoluted spectra analyzed by peak detection software. A mass window of interest is chosen and identifying peaks as potential glycan signals by comparison to theoretically predicted glycan masses. For each glycan peak above a certain threshold the signal of any peak at [M+2] is determined and the ratio [M+2]/[M] calculated. Glycan peaks with an increased [M+2]/[M] ratio relative to one or more other similar glycans are then identified as sulfated glycans.

FIGS. 3A and 3B provide an example of such data and comparison. The [M+2]/[M] ratio of a glycan peak of a sulfated glycan ($NeuAc_1Fuc_1Gal_1Man_3GlcNAc_5Sulfate_2$ complex N-glycan) appearing in the mass window from about 2265 amu to about 2297 amu is compared to the [M+2]/[M] ratio of a glycan peak of an unsulfated glycan ($NeuAc_1Fuc_1Gal_3Man_3GlcNAc_5$ complex N-linked glycan), in the mass window from about 2430 amu to about 2462 amu. The [M+2]/[M] ratio of the sulfated glycan was about 0.091 (or 91%) and that of a similar unsulfated glycan was about 0.75 (75%) and the sulfated glycan [M+2]/[M] ratio is both greater than the unsulfated [M+2]/[M] ratio by about 0.16 and by a factor of greater than about 1.2, identifying the glycan in the about 2265 amu to about 2297 amu as a sulfated glycan.

REFERENCES (1) Jiang, Hui; Irungu, Janet; Desaire, Heather. "Enhanced detection of sulfated glycosylation sites in glycoproteins," J. Amer. Soc. Mass Spectrom. (2005), 16(3), pp. 340-348.

(2) Irungu, Janet; Dalpathado, Dilusha S.; Go, Eden P.; Jiang, Hui; Ha, Hy-Vy; Bousfield, George R.; Desaire, Heather. Method for Characterizing Sulfated Glycoproteins in a Glycosylation Site-Specific Fashion, "Using Ion Pairing and Tandem Mass Spectrometry," Anal. Chem. (2006), 78(4), pp. 1181-1190.

(3) Balagurunathan Kuberan, Miroslaw Lech, Lijuan Zhang, Zhengliang L. Wu, David L. Beeler, and Robert D. Rosenberg, "Analysis of Heparan Sulfate Oligosaccharides with Ion Pair-Reverse Phase Capillary High Performance Liquid Chromatography-Microelectrospray Ionization Time-of-Flight Mass Spectrometry" J. Am. Chem. Soc. (2002), 124, pp. 8707-8718.

(4) Shi, D.-H. Stone, Hendrickson, Chistopher L., and Marshall, Alan G., "Counting individual sulfur atoms in a protein by ultrahigh-resolution Fourier transform ion cyclotron resonance mass spectrometry: Experimental resolution of isotopic fine structure in proteins," Proc. Natl. Acad. Sci., (1998), 95, pp. 11532-11537.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the present disclosure has been described in conjunction with various embodiments and examples, it is not intended that the present inventions be limited to such embodiments or examples. On the contrary, the present disclosure encompasses various alternatives, modifications, and equivalents, as will be appreciated by those of skill in the art.

While the present disclosure has been particularly shown and described with reference to specific illustrative embodiments, it should be understood that various changes in form and detail may be made without departing from the spirit and scope of the present disclosure. Therefore, all embodiments that come within the scope and spirit of the present disclosure, and equivalents thereto, are intended to be claimed. The claims, descriptions and diagrams of the methods, systems, and assays of the present disclosure should not be read as limited to the described order of elements unless stated to that effect.

What is claimed is:

1. A method for identifying sulfated glycans in a mixture of glycans, comprising the steps of: providing a mass spectrum for a mixture of glycans; determining for multiple pairs of mass peaks in the mass spectrum separated by two mass units, [M] and [M+2], the signal strength ratio [M+2]/[M] for each pair; and identifying a mass peak associated with a first glycan as that of a sulfated glycan when at least the [M+2]/[M] ratio associated with the first glycan is greater than the [M+2]/[M] ratio associated with mass peaks corresponding to one or more similar glycans by a selected threshold.

2. The method of claim 1, wherein the mixture of glycans comprises one or more of free glycans, derivatized glycans, enzymatically-treated glycans, cleavage product glycans, and glycans bound to a substantially intact protein, peptide, or lipid, and mixtures comprising combinations thereof.

3. The method of claim 1, wherein the mixture of glycans comprises sulfated glycans and phosphorylated glycans.

4. The method of claim 1, comprising identifying the presence of a specific glycan of interest when at least the [M+2]/[M] ratio associated with the mass peak of the specific glycan is greater than the [M+2]/[M] ratio associated with mass peaks corresponding to one or more similar glycans by a selected threshold.

5. The method of claim 1, wherein the one or more similar glycans are from substantially the same glycan family as the first glycan.

6. The method of claim 1, wherein the one or more similar glycans have masses within about ±20% of the mass of the first glycan.

7. The method of claim 1, wherein the selected threshold is a [M+2]/[M] ratio associated with the first glycan that is greater than about 1.1 times the [M+2]/[M] ratio of one or more of the similar glycans.

8. The method of claim 1, wherein the selected threshold is a [M+2]/[M] ratio associated with the first glycan that is greater than the [M+2]/[M] ratio of one or more of the similar glycans by about 0.02.

9. The method of claim 1, wherein the glycans are from a glycoprotein sample, a protoglycan sample or a glycolipid sample.

10. The method of claim 1, wherein the signal strength is defined as the intensity of a mass peak, the total area under a mass peak or a percentage of the area under a mass peak.

11. A method for identifying sulfated glycans in a mixture of glycans, comprising the steps of: providing a mass spectrum for a mixture of glycans; determining for multiple pairs of mass peaks in the mass spectrum separated by two mass units, [M] and [M+2], the signal strength ratio [M+2]/[M] for each pair; and identifying a mass peak as arising from a sulfated glycan based at least on the distribution of [M+2]/[M] ratios for three or more similar glycans.

12. The method of claim 11, wherein the step of identifying a mass peak as arising from a sulfated glycan comprises identifying as sulfated glycans mass peaks that have [M+2]/[M] ratios in the higher value mode of a bimodal distribution of [M+2]/[M] ratios for three or more similar glycans.

13. The method of claim 11, wherein the mixture of glycans comprises one or more of free glycans, derivatized glycans, enzymatically-treated glycans, cleavage product glycans, and glycans bound to a substantially intact protein, peptide, or lipid, and mixtures comprising combinations thereof.

14. The method of claim 11, wherein the mixture of glycans comprises sulfated glycans and phosphorylated glycans.

15. The method of claim 11, comprising identifying the presence of a specific glycan on interest when at least the [M+2]/[M] ratio associated with the mass peak of the specific glycan is greater than the [M+2]/[M] ratio associated with mass peaks corresponding to one or more similar glycans by a selected threshold.

16. The method of claim 11, wherein the one or more similar glycans are from substantially the same glycan family as the first glycan.

17. A method for identifying sulfated glycans in a mixture of glycans, comprising the steps of: providing a mass spectrum for a mixture of glycans; determining for at least one pair of mass peaks in the mass spectrum separated by two mass units, [M] and [M+2], the signal strength ratio [M+2]/[M]; and identifying a mass peak associated with the glycan as that of a sulfated glycan when at least the [M+2]/[M] associated with the glycan is similar to the [M+2]/[M] of a computer-generated mass spectra for a theoretical sulfated glycan.

18. The method of claim 17, wherein the determined [M+2]/[M] ratio associated with the glycan is similar to the [M+2]/[M] ratio of a computer-generated mass spectra for a theoretical sulfated glycan when the determined and computer-generated mass ratios are within about ±20% of each other.

19. The method of claim 1, wherein the glycans are from a therapeutic formulation, a body fluid, a cell surface material, an extracellular matrix, an intracellular material, a tissue culture, a bioreactor, a human or animal tissue, or a plant.

20. The method of claim 1, wherein the glycans are linear or branched carbohydrates.

* * * * *